(12) United States Patent
Akagane

(10) Patent No.: US 12,171,454 B2
(45) Date of Patent: Dec. 24, 2024

(54) CURVED ULTRASONIC TRANSMISSION MEMBER HAVING IMPROVED VIBRATION CONTROL

(71) Applicant: OLYMPUS CORPORATION, Tokyo (JP)

(72) Inventor: Tsunetaka Akagane, Hachioji (JP)

(73) Assignee: Olympus Corporation, Tokyo (JP)

( * ) Notice: Subject to any disclaimer, the term of this patent is extended or adjusted under 35 U.S.C. 154(b) by 522 days.

(21) Appl. No.: 17/577,616

(22) Filed: Jan. 18, 2022

(65) Prior Publication Data

US 2022/0265304 A1    Aug. 25, 2022

Related U.S. Application Data

(60) Provisional application No. 63/153,540, filed on Feb. 25, 2021.

(51) Int. Cl.
*A61B 17/32* (2006.01)
*A61B 17/00* (2006.01)

(52) U.S. Cl.
CPC ......... *A61B 17/320068* (2013.01); *A61B 2017/00526* (2013.01); *A61B 2017/320073* (2017.08); *A61B 2017/320089* (2017.08)

(58) Field of Classification Search
CPC ........... A61B 17/320068; A61B 2017/320073; A61B 2017/320089; A61B 2017/00526
See application file for complete search history.

(56) References Cited

U.S. PATENT DOCUMENTS

| | | | |
|---|---|---|---|
| 5,318,570 A * | 6/1994 | Hood | A61B 17/8847 601/2 |
| 6,328,751 B1 | 12/2001 | Beaupre | |
| 11,020,140 B2 * | 6/2021 | Gee | A61B 17/320092 |
| 2005/0203418 A1 | 9/2005 | Yamada et al. | |
| 2009/0143806 A1 | 6/2009 | Witt et al. | |
| 2017/0143371 A1 | 5/2017 | Witt et al. | |
| 2017/0143877 A1 | 5/2017 | Witt et al. | |
| 2017/0196586 A1 | 7/2017 | Witt et al. | |
| 2017/0196587 A1 | 7/2017 | Witt et al. | |
| 2017/0202573 A1 | 7/2017 | Witt et al. | |

(Continued)

FOREIGN PATENT DOCUMENTS

| | | |
|---|---|---|
| JP | 4249064 B2 | 4/2009 |
| JP | 2011-505198 A | 2/2011 |

(Continued)

*Primary Examiner* — Ashley L Fishback

(74) *Attorney, Agent, or Firm* — Morgan, Lewis & Bockius LLP

(57) ABSTRACT

A vibration transmission member for an ultrasonic treatment tool includes: a main body including a central axis, a distal end (DE), and a proximal end (PE), a center moving portion (CMP) at a distal side of a node where the DE meets the CMP, the node being at a most DE of the main body, and a curved portion (CP) at a distal side of the CMP. In a direction from a PE of the CP toward a DE of the CP, the CP is curved in a first direction. The center of gravity of the CMP moves along the CMP toward the DE of the CMP, the center of gravity moves relative to the central axis in a second direction. The CP extends from the DE of the main body to the PE of the CP. The CP includes a plurality of notches along a periphery of the CP.

20 Claims, 13 Drawing Sheets

(56) References Cited

U.S. PATENT DOCUMENTS

| | | |
|---|---|---|
| 2018/0263653 A1 | 9/2018 | Witt et al. |
| 2018/0289389 A1 | 10/2018 | Witt et al. |
| 2019/0142450 A1 | 5/2019 | Shimamura et al. |
| 2019/0183522 A1 | 6/2019 | Akagane |
| 2019/0239919 A1 | 8/2019 | Witt et al. |
| 2020/0029997 A1 | 1/2020 | Shimamura et al. |
| 2020/0046401 A1 | 2/2020 | Witt et al. |

FOREIGN PATENT DOCUMENTS

| | | |
|---|---|---|
| WO | 2018/011896 A1 | 1/2018 |
| WO | 2018/037478 A1 | 3/2018 |

* cited by examiner

CURVED ULTRASONIC TRANSMISSION MEMBER HAVING IMPROVED VIBRATION CONTROL

RELATED APPLICATION DATA

This application is based on and claims priority under 35 U.S.C. § 119 to U.S. Provisional Application No. 63/153,540, filed Feb. 25, 2021, the entire contents of which are incorporated herein by reference.

FIELD OF THE INVENTION

The present invention relates to an ultrasonic actuated unit including a vibration transmission member that extends along a longitudinal axis and which can transmit an ultrasonic vibration from a proximal direction toward a distal direction, wherein the ultrasonic actuated unit is actuated when the ultrasonic vibration is transmitted. The present invention also relates to an ultrasonic treatment device including the ultrasonic actuated unit.

DESCRIPTION OF THE RELATED ART

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art against the present invention.

Japanese PCT National Publication No. 2011-505198 discloses an ultrasonic scalpel and an electrosurgical device. This ultrasonic scalpel is vibrated at a high frequency (for example, 55,500 times per second) to denature protein in tissue. Furthermore, a blood vessel is squashed by the combination of a pressure applied by a blade surface to tissue, and a clamping mechanism, so that a coagulum forms a hemostatic seal.

Japanese Patent No. 4249064 has disclosed an ultrasonic actuated unit which is actuated when the ultrasonic vibration is transmitted. This ultrasonic actuated unit includes an ultrasonic transmitting portion which can transmit an ultrasonic vibration from a proximal direction toward a distal direction. The ultrasonic transmitting portion includes a horn member serving as a proximal-side transmitting member to which an ultrasonic vibrator that is an ultrasonic generating portion is attached, and a probe serving as a distal-side transmitting member which is connected to the distal direction side of the horn member. The ultrasonic transmitting portion is inserted through a channel of an endoscope. A distal treatment section is provided in a distal portion of the probe, and when the ultrasonic vibration is transmitted to the distal treatment section, a treatment target such as a living tissue is treated by the use of the ultrasonic vibration. When the ultrasonic vibration is transmitted, the ultrasonic transmitting portion performs a longitudinal vibration having a vibration direction parallel to the longitudinal axis at a predetermined reference frequency.

A vibration absorbing member is disposed on an outer peripheral portion of the probe of the ultrasonic transmitting portion at a node position of the longitudinal vibration. The vibration absorbing member is in abutment with an inner peripheral portion of the channel. Here, in the ultrasonic actuated unit, the shape of the ultrasonic transmitting portion about the longitudinal axis may be partly asymmetric, or the material quality of the ultrasonic transmitting portion may be partly nonuniform. In this case, in addition to the longitudinal vibration, an imprecise vibration having a vibration direction which is not parallel to the longitudinal axis is generated. When the imprecise vibration is generated, the imprecise vibration is absorbed by the vibration absorbing member. Because the vibration absorbing member is located at the node position of the longitudinal vibration, the longitudinal vibration is not absorbed by the vibration absorbing member.

International Application No. PCT/JP2016/074509 discloses a related art surgical treatment device, which will be described with reference to FIGS. 1-3. FIG. 1 is a schematic diagram showing the entire configuration of a surgical treatment device according to a related art device. FIG. 2 is a perspective view showing a distal portion of a probe and a jaw of a handpiece in the surgical treatment device shown in FIG. 1. FIG. 3 is a cross-sectional view showing a vibrator unit in the surgical treatment device shown in FIG. 1.

As shown in FIGS. 1-3, a related art surgical treatment device 11 includes a handpiece 12, a vibrator unit 13 that is detachably attachable with respect to the handpiece 12, a power source unit 14, and a cable 15 that connects the handpiece 12 and the power source unit 14. The vibrator unit 13 includes a case 16 and a vibration generator (transducer) 18 housed in the case 16 that is detachably attachable with respect to a housing 17.

As shown in FIGS. 1-3, the handpiece 12 includes: the housing 17 that forms an outer shell; a fixed handle 21 that is provided integrally with the housing 17; a handle 22 that is rotatable with respect to the housing 17; a plurality of operation buttons 23 that are provided in the housing 17; a rod-shaped probe 24 (treatment portion, an ultrasonic probe) that is connected to the vibration generator 18 in the case 16; a cylindrically-shaped shaft 25 that covers the periphery of the probe (rod member) 24 in its proximal side to protect the probe 24; a knob for rotation (hereinafter, referred to as a rotation knob) 31 that is fixed to the shaft 25; a jaw 32 that is provided in a manner to be rotatable with respect to the probe 24 and the shaft 25; and a cylindrically-shaped advance-and-retreat portion 33 that is provided inside the shaft 25 and is caused to advance or retreat when the jaw 32 is opened or closed. One of the two directions parallel to a longitudinal direction L of the probe 24 is defined as a distal side, and the other direction opposite to the distal side is defined as a proximal side. The longitudinal direction L extends along a central axis C of the probe 24.

As shown in FIG. 3, the vibration generator 18 includes an ultrasonic vibrator 34 and a horn member 35. The ultrasonic vibrator 34 is provided with a plurality of piezoelectric elements 36 (for example, four piezoelectric elements 36, in the shown embodiment) that convert current into ultrasonic vibration. The ultrasonic vibrator 34 is connected to an electric wire 37. The electric wire 37 extends through the inside of the cable 15, and is connected to an ultrasonic current supply portion 38 in the power source unit 14 at the other end. When electric power is supplied from the ultrasonic current supply portion to the ultrasonic vibrator 34 via the electric wire 37, ultrasonic vibration is generated in the ultrasonic vibrator 34.

As shown in FIG. 3, the ultrasonic vibrator 34 is attached to the horn member 35. The horn member 35 is made of a metal material, for example. The horn member 35 has a substantially conically shaped portion that decreases in cross section from the base end towards the apex end, i.e., towards the distal side of the probe 24. Ultrasonic vibration generated in the ultrasonic vibrator 34 is so-called longitudinal vibration, and a vibration direction of this vibration corresponds to the longitudinal direction L of the probe 24. The amplitude of the ultrasonic vibration is expanded in the cross-section change portion of the horn member 35.

As shown in FIG. 2, the shaft 25 is formed in a cylindrical shape and protects the probe 24 placed inside the shaft 25. The shaft 25 is attached to the housing 17 rotatably with respect to the housing 17, on the proximal side. The rotation knob 31 is provided to be fixed to the shaft 25. By rotating the rotation knob 31 with respect to the housing 17, the shaft 25, the probe 24, the ultrasonic vibrator 34, and the jaw 32 can be rotated integrally around the central axis C. The shaft 25 includes a support pin 41 for supporting the jaw 32 in the distal portion 42.

As indicated by the arrow in FIG. 2, the jaw 32 is rotatable about the support pin 41 between a facing position where the jaw 32 is moved to bear against the probe 24 and a separate position (as shown in FIG. 2) where the jaw 32 is separate from the probe 24. An operator can open and close the jaw 32 by rotating the handle 22 with respect to the housing 17. That is, when an operator operates the handle 22, the advance-and-retreat portion 33 provided inside the shaft 25 advances or retreats along the central axis C of the shaft 25, thereby opening or closing the jaw 32.

As shown in FIG. 2, the probe 24 (treatment portion) is made of, for example, a biocompatible metal material (e.g., a titanium alloy) in a rod-like shape that is curved in a manner such that the distal side of the probe 24 is laterally displaced with respect to the central axis C. An ultrasonic vibration (ultrasonic energy) that is transmitted to the probe 24 enables the probe 24 to treat biological tissue. The probe 24 includes, in its longitudinal direction L, the distal portion 42 located on the distal side and a proximal portion 43 (see FIG. 3) on the side opposite to the distal portion 42. The probe 24 includes, in a circumferential direction, a treatment surface 45 for performing treatment, such as coagulation treatment or coagulation-and-incision treatment with respect to biological tissue, and an opposite surface 46 on the side opposite to the treatment surface 45.

The probe 24 includes the treatment surface 45 that treats biological tissue. The probe 24 is formed in a manner such that its cross-sectional shape forms an octagon, in which, for example, three surfaces that face the jaw 32 constitute the treatment surface 45, while three surfaces that face the treatment surface 45 constitute the opposite surface 46. A pair of side surfaces 47 is provided between the treatment surface 45 and the opposite surface 46.

As shown in FIG. 1, the power source unit 14 includes the ultrasonic current supply portion 38 and the controller 65 that controls the ultrasonic current supply portion 38. The controller 65 can control supply of electric power from the ultrasonic current supply portion 38 to the ultrasonic vibrator 34. When an operator operates the operation buttons 23, the controller 65 supplies current from the ultrasonic current supply portion 38 to the vibration generator 18.

The plurality of operation buttons 23 include a first operation button 23A corresponding to a coagulation mode and a second operation button 23B corresponding to a coagulation-and-incision mode. Therefore, for example, when an operator operates the first operation button 23A, the probe 24 outputs ultrasonic energy suitable for coagulation of biological tissue under control of the aforementioned controller 65. For example, when an operator operates the second operation button 23B, the probe 24 outputs ultrasonic energy suitable for coagulation and incision of biological tissue under control of the controller 65.

FIG. 4A is a side view of a related art ultrasonic probe in which notches are cut to provide treatment surfaces. FIG. 4B is a top view of a portion of the probe of FIG. 4A. FIG. 4C is a bottom view of a portion of the probe of FIG. 4A.

As shown with reference to FIGS. 4A-4C, a probe 24 is formed with first to fourth pairs of notches 51, 52, 53, 54 to obtain the octagonal cross-sectional shape with the surfaces 45, 46, 47 (see FIG. 2). The notches may be facets along and defining each of the surfaces 45, 46, 47. The related art probe 24 includes the first pair of notches 51, which form the side surfaces 47. The first pair of notches 51 are symmetrical on both sides of the probe 24, and begin closer to the proximal portion 43 of the probe 24 than the second to fourth notches 52, 53, 54 forming the treatment surface 45 and the opposite surface 46. The first pair of notches 51 extend furthest toward the proximal end of the probe 24 among the first to fourth notches 51, 52, 53, 54 (e.g., 54a, 54b).

The fourth pair of notches 54 includes a top notch 54a and a bottom notch 54b, which are opposed to one another. The top notch 54a is on the top of the probe 24, and is a center surface among the three surfaces of the treatment surface 45. The bottom notch 54b is on the bottom of the probe 24, and is a center surface among the three surfaces that constitute the opposite surface 46. The top notch 54a extends second furthest, and the bottom notch 54b extends third furthest toward the proximal end of the probe 24 among the first to fourth pairs of notches 51, 52, 53, 54 (e.g., 54a, 54b).

The second pair of second notches 52, which are two side surfaces among the three surfaces of the treatment surface 45, on opposite sides of the top notch 54a, extend fourth furthest toward the proximal end of the probe 24 among the first to fourth pairs of notches 51, 52, 53, 54 (e.g., 54a, 54b). The third pair of notches 53, which are two side surfaces among the three surfaces of the opposite surface 46, on opposite sides of the bottom notch 54b, extend fifth furthest (least) toward the proximal end of the probe 24 among the first to fourth pairs of notches 51, 52, 53, 54 (e.g., 54a, 54b).

With further reference to FIGS. 4A-4C, each cross section taken along lines IV-IV', V-V', and VI-VI' of the probe 24 of FIG. 4A has a different shape. FIG. 4A shows that a most distal cross section, taken along line IV-IV', closest to the distal end 42, has an octagonal cross section due to the presence of all of the first to fourth pairs of notches 51, 52, 53, 54 (e.g., 54a, 54b). In a middle cross section, taken along line V-V', only the first pair of notches 51 are present, and this middle cross section has a quadrilateral-like (four-sided) cross-section consisting of two sides formed by the first pair of notches 51 and a top and a bottom that are curved sections joining the two sides. A most proximal cross section, taken along line VI-VI', closest to the proximal end 43, has a circular cross section, with no notches present.

FIG. 5A is a diagram showing strain amounts and directions on the probe of FIG. 4A.

The distal portion 42 of the probe 24 is curved in one direction to improve visibility during treatment of a patient by a clinician. However, when the probe 24 is curved, there is a problem in that imprecise vibration occurs and the ultrasonic vibration is not stable. Imprecise vibration includes transverse vibration and twist vibration. The transverse vibration (TRV) is in one direction, perpendicular to the longitudinal vibration (LV). The twist vibration (TWV) twists around the longitudinal direction. As shown in FIG. 5A, the forces due to the transverse and twist vibration tend to deform the probe and create an unstable vibration.

FIG. 5B is another side view of the probe of FIG. 4A and annotating the curvature of the related art probe. With reference to FIG. 5B, a main body 70 is at the proximal side of the related art probe 24. A center moving portion 71 of the probe 24 is a taper portion, and is separated from the main body by a node 72. Within the probe 24, the center moving portion 71 is located more distal than the node 72, which itself is at the most distal side of the main body 70, e.g., further toward the distal end. The surface of the center moving portion 71 has a taper portion in which the taper is formed approaching the central axis C toward the distal end, i.e., inwardly (toward the central axis C) and distally (toward the distal end). A curved portion 73 is more distal than the center moving portion 71. Taken together, the movement of the center of gravity in the center moving portion 71 and the curved portion 73 has a discontinuous curvature, with the curvature in the center moving portion 71 and curved portion 73, interrupted by at least one non-curved section, i.e. section 75. In FIG. 5B, arrow A represents the direction and orientation of the movement of the center of gravity of the probe 24 in the center moving portion 71, and arrows B-D represent the direction and orientation of the movement of the center of gravity of the probe 24 in the curved portion 73. The second arrow B, representing the direction and orientation of the movement of the center of gravity of the probe 24 in section 75, shows a plateau section, which causes the discontinuous curvature of the probe 24. The discontinuity is caused by the relative lengths of the first to fourth notches 51-54.

Along the length of the probe 24, the center of gravity of the probe 24 moves relative to the central axis C. For example, in the center moving portion 71, the center of gravity of the probe 24 moves, e.g., can be measured or determined as a function of position along the center axis, in a first direction (FD), e.g., toward the outside of the curve of the probe 24, as the longitudinal position moves distally from a location proximate the node 72 toward and into a first proximal portion of the center moving portion 71. The taper portion in the configuration described above causes the described movement in the center of gravity in the center moving portion 71. Also for example, in the curved portion 73, the center of gravity of the probe 24 first is non-varying with respect to the center axis (see section 75), and then moves (can be measured or determined) in first direction (FD), e.g., toward the outside of the curve of the probe 24, and then in a second direction (SD), e.g., toward the inside of the curve of the probe 24, as the longitudinal position moves distally from the first proximal portion of the center moving portion 71 toward the distal end of the probe 100 at the tip 74. The inclusion of the non-varying section 75 between the center moving portion 71 and the first to fourth pairs of notches 51, 52, 53, 54 in the configuration described above causes the described discontinuous movement in the center of gravity. As such, the center of gravity of the probe 24 moves discontinuously toward the outside of the curve of the probe 24 as the longitudinal position moves distally in the center moving portion 71 through the beginning section of the curved portion 73, e.g., through section 75 and the location where the first to fourth pairs of notches 51, 52, 53, 54 begin in the configuration described above, and, thereafter, the center of gravity of the probe 24 moves continuously toward the inside of the curve of the probe 24 as the longitudinal position moves distally in the curved portion 73.

SUMMARY OF THE INVENTION

Accordingly, the present disclosure is directed to a vibration transmission member, which substantially obviates one or more of the issues due to limitations and disadvantages of the related art vibration transmission member.

An object of the present disclosure is to provide a vibration transmission member for an ultrasonic treatment tool, including: a main body including a central axis and having a distal end and a proximal end, a center moving portion located at a distal side of a node located where the distal end of the main body meets the center moving portion, the node being at a most distal location of the distal end of the main body, and a curved portion located at a distal side of the center moving portion. In a direction from a proximal end of the curved portion toward a distal end of the curved portion, the curved portion is curved in a first direction relative to the central axis. The center moving portion has a center of gravity that is located in a cross section of the center moving portion. The center moving portion is configured so that as the center of gravity moves along a length of the center moving portion toward the distal end of the center moving portion, the center of gravity moves relative to the central axis in a second direction that is opposite to the first direction. The center moving portion extends from the distal end of the main body to the proximal end of the curved portion. The curved portion includes a plurality of notches formed along a periphery of the curved portion.

Another object of the present disclosure is to provide a vibration transmission probe for an ultrasonic treatment tool, including: a distal end and a proximal end, the distal end being at a tip of the probe, a treatment surface for performing an ultrasonic treatment, the treatment surface including first to third surfaces, an opposite surface, opposite to the treatment surface, the opposite surface including fourth to sixth surfaces, and seventh and eighth surfaces respectively on each side of the probe between the treatment surface and the opposite surface. The seventh and eighth surfaces include a first pair of notches. The first and third surfaces include a second pair of notches. The fourth and sixth surfaces include a third pair of notches. The second surface is between the first and third surfaces and includes a top notch. The fifth surface is between the fourth and sixth surfaces and includes a bottom notch. The top notch extends furthest toward the proximal end among the notches. The bottom notch extends least toward the proximal end among the notches.

Still another object of the present disclosure is to provide a vibration transmission probe for an ultrasonic treatment tool, including: a distal end and a proximal end, the distal end being at a tip of the probe, a distal portion closest to the distal end, the distal portion having a cross section having an octagonal cross section due to the presence of first to fourth pairs of notches, the fourth pair of notches including a top notch and a bottom notch, a middle portion of the probe having a cross section having a six-sided cross-section, such that only the top notch, the second pair of notches, and the first pair of notches extend from the distal section to the middle section, and a proximal portion closest to the proximal end, the proximal portion having a circular cross section, such that no notches extend into the proximal portion.

Yet another object of the present disclosure is to provide a vibration transmission probe for an ultrasonic treatment tool, including: a distal end and a proximal end, the distal end being at a tip of the probe, a main body at the proximal end, a center moving portion including a taper portion, the center moving portion being separated from the main body by a node, the center moving portion being located more distal than the node, the node being at the most distal side of the main body toward the distal end, the taper portion in which a taper is formed approaching a central axis of the probe toward the distal end, inwardly toward the central axis and distally toward the distal end, and a curved portion more distal than the center moving portion, the curved portion continuing to taper, inwardly and distally, toward the tip at the distal end, the curvature of the curved portion being a simple curvature, having a continuous curvature, such that a center of gravity of the probe moves relative to the central axis.

Additional features and advantages will be set forth in the description that follows, and in part will be apparent from the description, or may be learned by practice of the invention. The objectives and other advantages of the disclosed vibration transmission member will be realized and attained by the structure particularly pointed out in the written description and claims thereof as well as the appended drawings.

BRIEF DESCRIPTION OF THE DRAWINGS

The accompanying drawings, that may be included to provide a further understanding of the disclosure and are incorporated in and constitute a part of this specification, illustrate embodiments of the disclosure and together with the description serve to explain various principles of the disclosure. The following detailed description of preferred embodiments can be read in connection with the accompanying drawings in which like numerals designate like elements.

Figure 1:
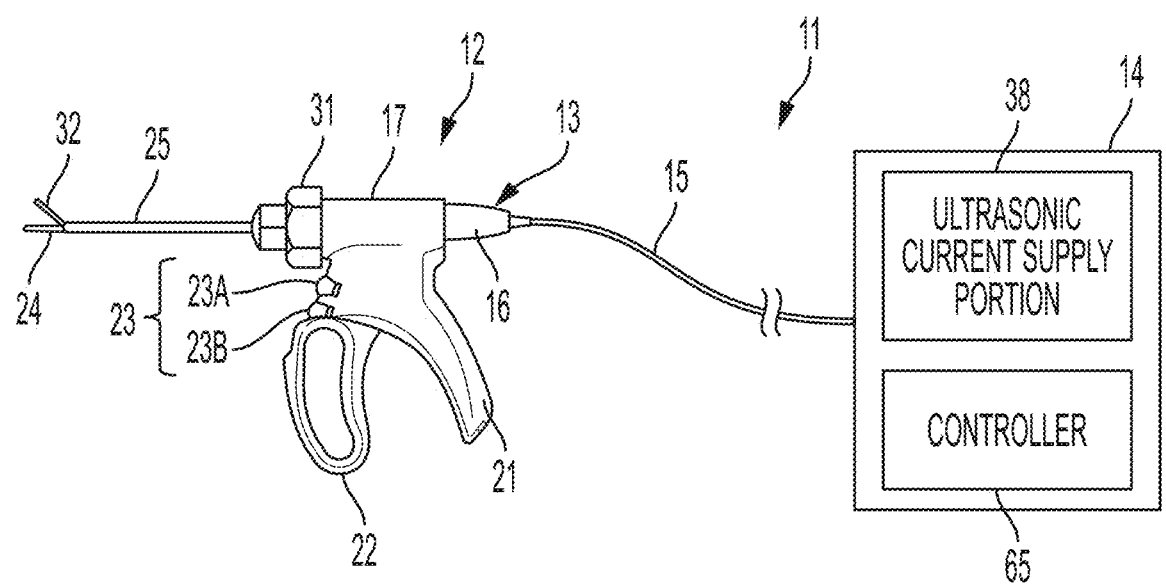
FIG. 1 is a schematic diagram showing the entire configuration of a surgical treatment device according to a related art device.
Figure 2:
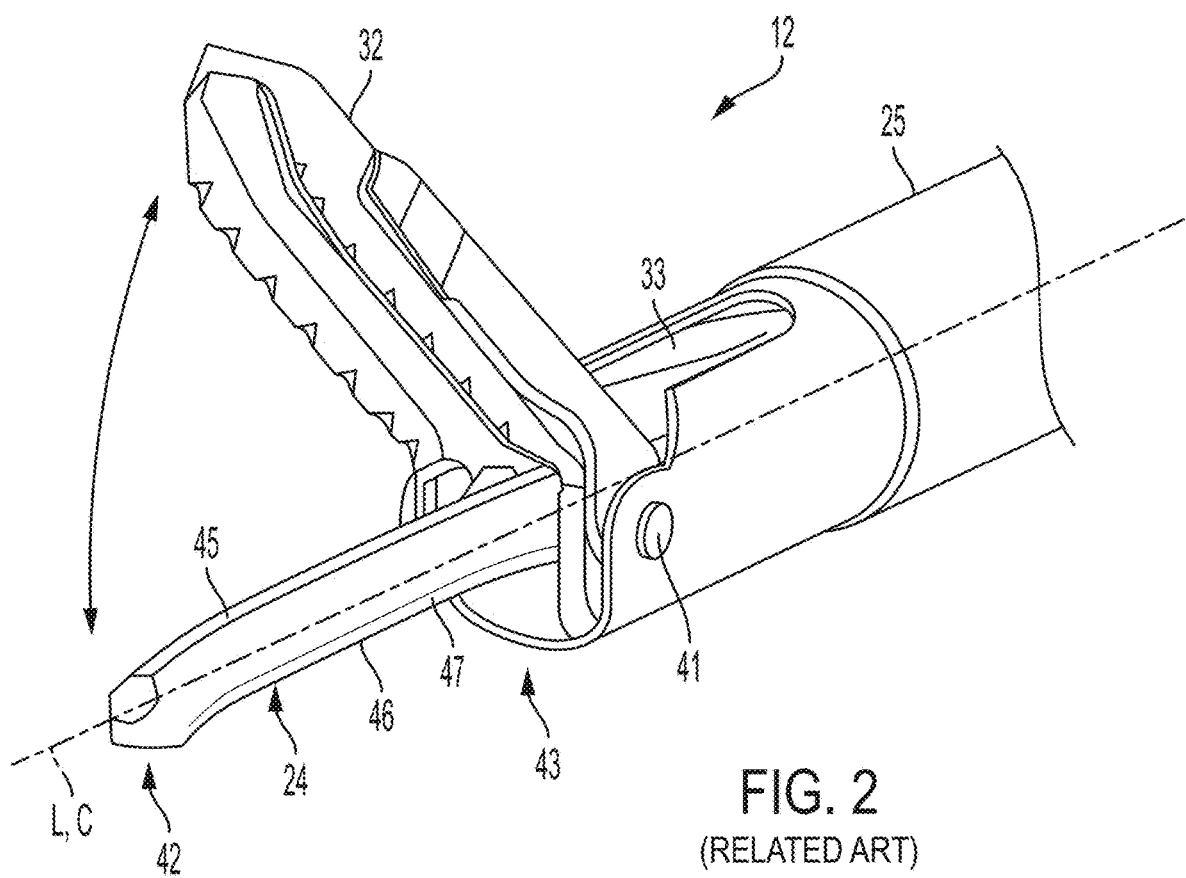
FIG. 2 is a perspective view showing a distal portion of a probe and a jaw of a handpiece in the surgical treatment device shown in FIG. 1.
Figure 3:
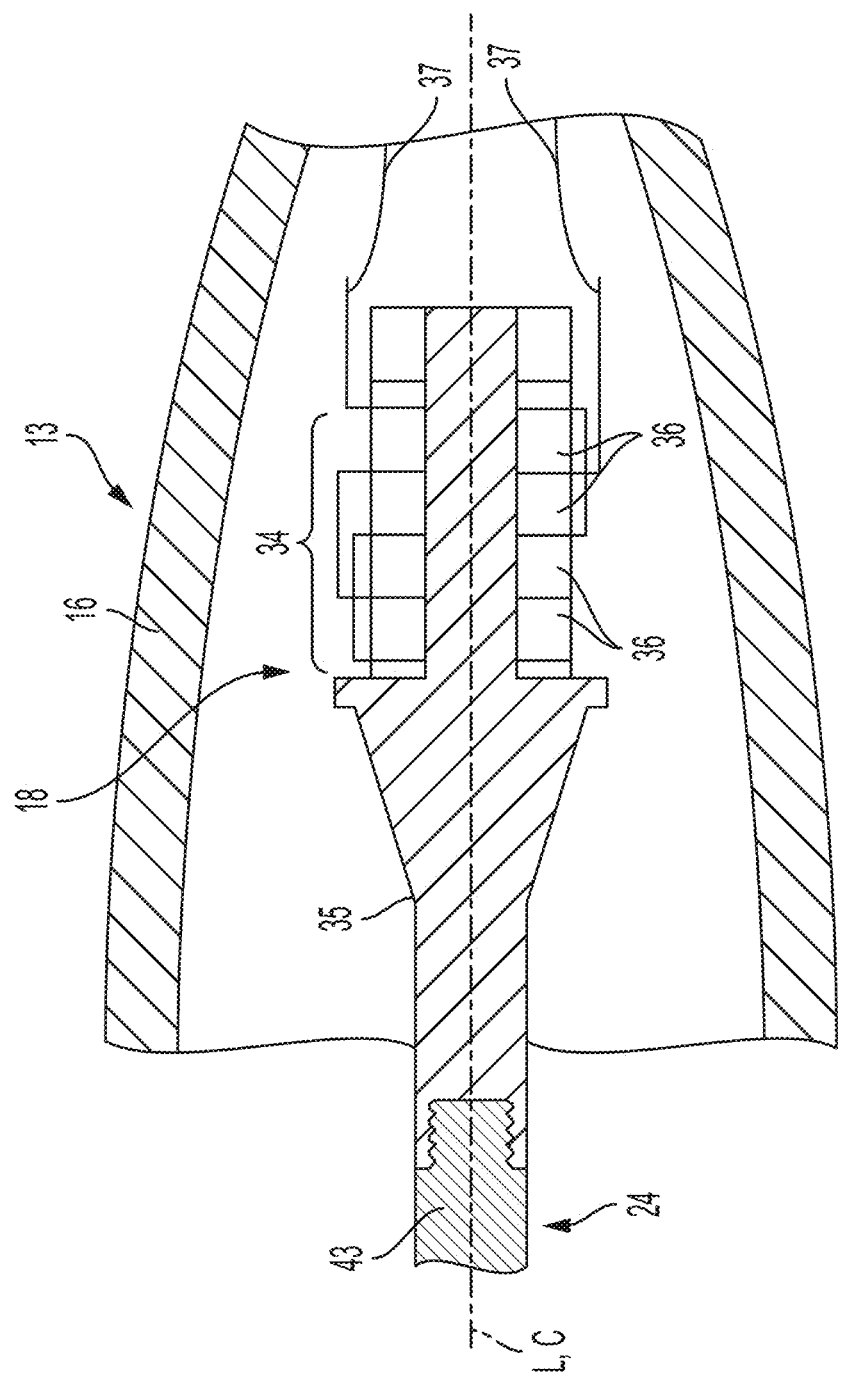
FIG. 3 is a cross-sectional view showing a vibrator unit in the surgical treatment device shown in FIG. 1.

For ease of viewing, in some instances only some of the named features in the figures are labeled with reference numerals. Throughout the drawings and the detailed description, unless otherwise described, the same drawing reference numerals should be understood to refer to the same elements, features, and structures. The relative size and depiction of these elements may be adjusted for clarity, illustration, and convenience.

DETAILED DESCRIPTION

Hereinafter, accompanying drawings, which are incorporated in and constitute a part of the specification, illustrate embodiments of the invention, and together with the general description given above and the detailed description of the embodiments given below, serve to explain the principles of the invention.

It should be noted that references throughout this disclosure to the terms "distal" and "distally" are to a direction away from the handle 21 (see FIG. 1), while references to the terms "proximal" and "proximally" are to a direction towards the clip operating part 16. Also, the term "patient," as used herein, comprises any and all organisms and includes the term "subject." A patient can be a human or an animal.

Figure 6A:
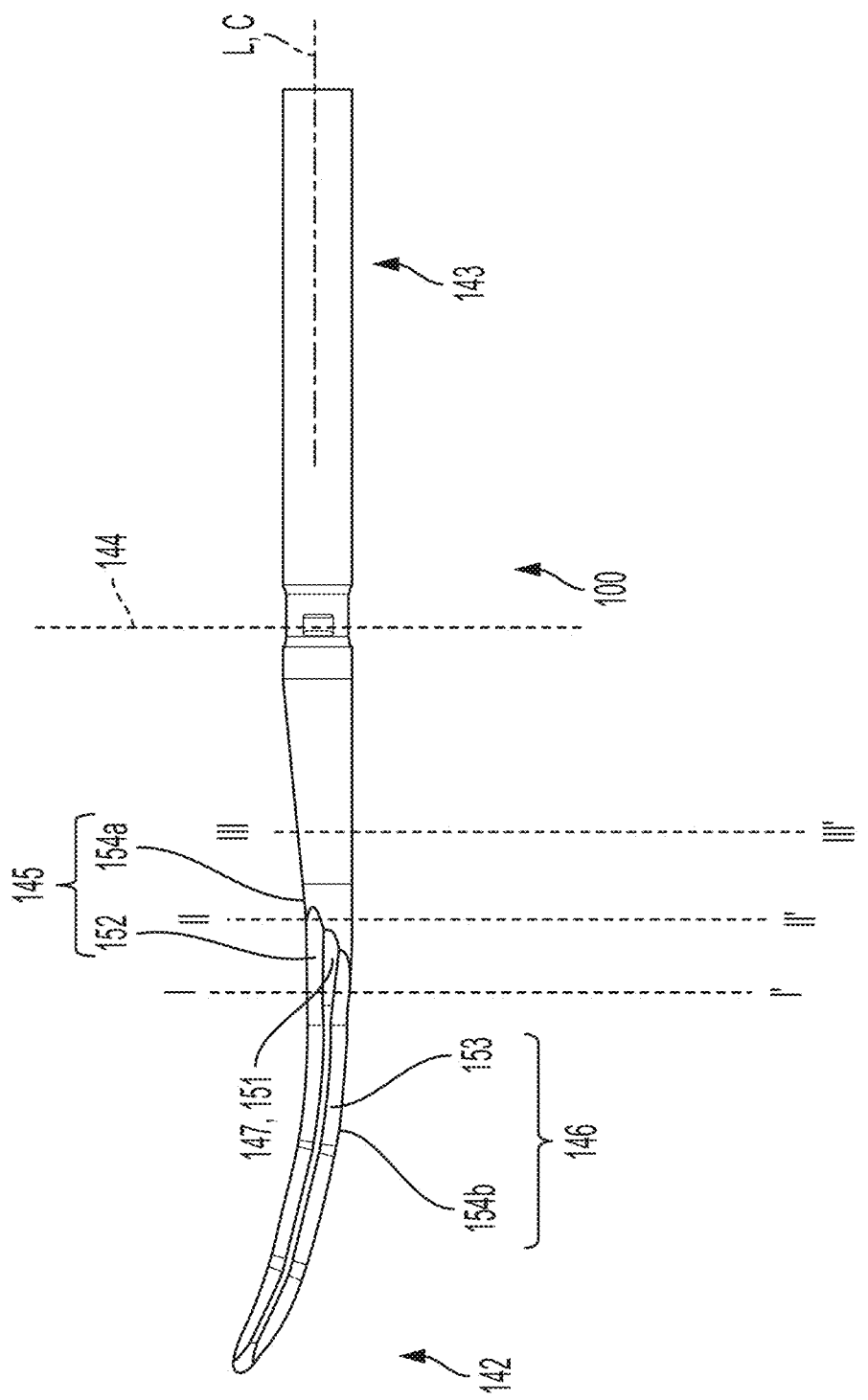
FIG. 6A is a side view of an ultrasonic probe in accordance with an example embodiment.
Figure 6B:
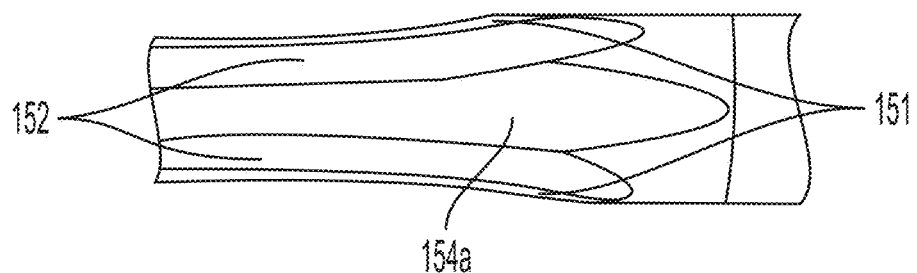
FIG. 6B is a top view of a portion of the probe of FIG. 6A.
Figure 6C:
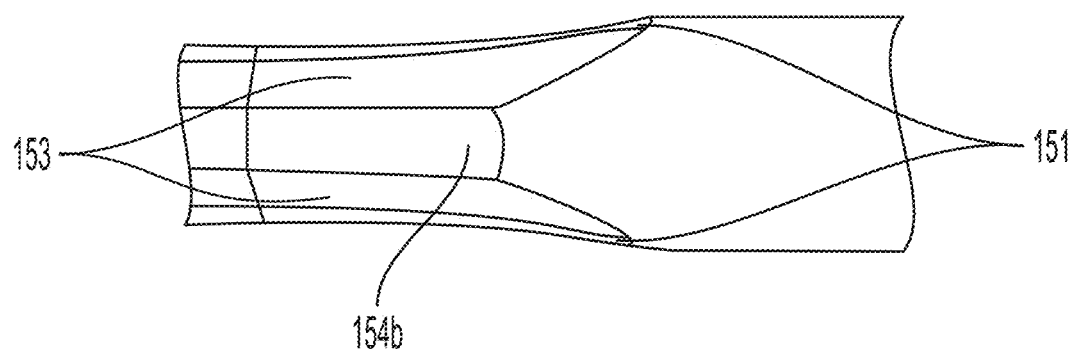
FIG. 6C is a bottom view of a portion of the probe of FIG. 6A.

FIGS. 6A-6C show various aspects and surfaces of an example embodiment of an ultrasonic probe. FIG. 6A is a side view of an ultrasonic probe in accordance with an example embodiment. FIG. 6B is a top view of a portion of the probe of FIG. 6A. FIG. 6C is a bottom view of a portion of the probe of FIG. 6A.

With reference to FIGS. 6A-6C, a probe 100 may be made of, for example, a biocompatible metal material (e.g., a titanium alloy) in a rod-like shape that may be curved in a manner such that the distal side of the probe 100 is laterally displaced with respect to a central axis C. An ultrasonic vibration (ultrasonic energy) may be transmitted to the probe 100 that enables the probe 100 to treat biological tissue. The probe 100 includes, in a longitudinal direction L along a central axis C, a distal end 142 located on a distal side (toward a tip of the probe, furthest from a handle, e.g., the handle 21 of FIG. 1) of a node 144 and a proximal end 143 on the side of the node 144 opposite to the distal end 142 (closest to the handle, e.g., the handle 21 of FIG. 1). The probe 100 includes, in a circumferential direction, a treatment surface 145 for performing a treatment, such as coagulation treatment or coagulation-and-incision treatment with respect to biological tissue, and an opposite surface 146 on the side opposite to the treatment surface 145. The probe 100 may be used in the handpiece 12 of FIG. 1 in place of the related art probe 24.

Figure 7A:
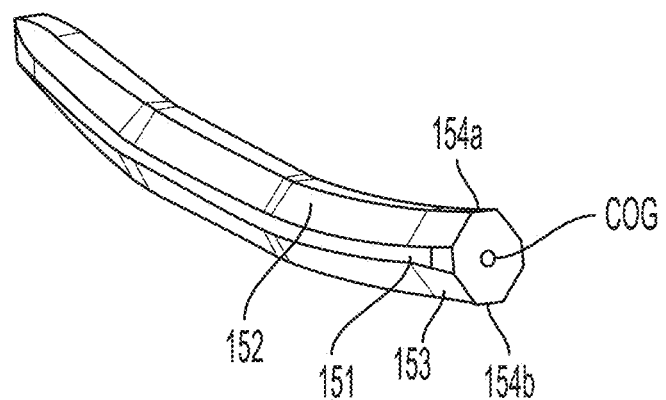
FIG. 7A is a cross-sectional view of the probe of FIG. 6A, taken along line I-I'.

The probe 100, and in particular the surfaces of the probe 100 forming the treatment surface 145 and the opposite surface 146, is formed in a manner such that its cross-sectional shape forms a polygon or curved shape. In one embodiment and as shown in FIG. 7A, the cross-sectional shape forms an octagon (although other polygonal and curved shapes can be used), in which, for example, three (e.g., first to third) surfaces that face a jaw constitute the treatment surface 145, while three (e.g., fourth to sixth) surfaces that face the treatment surface 145 constitute the opposite surface 146. A pair of side surfaces 147, e.g., seventh and eighth surfaces of the octagonal cross-section, are provided between the treatment surface 145 and the opposite surface 146.

As shown in FIGS. 6A-C, the probe 100 according to an embodiment is formed with first to fourth pairs of notches 151, 152, 153, 154 to obtain the octagonal cross-sectional shape with the surfaces 145, 146, 147. The probe 100 includes the first pair of notches 151, which form the side surfaces 147. The first pair of notches 151 may be symmetrical on both sides of the probe 100.

The fourth pair of notches 154 include a top notch 154a and a bottom notch 154b, which are opposed to one another. The top notch 154a is on the top of the probe 100, and is the center portion of the treatment surface 145. The bottom notch 154b is on the bottom of the probe 100, and is the center portion of the opposite surface 146. The top notch 154a extends furthest toward the proximal end of the probe 100 among the first to fourth pairs of notches 151, 152, 153, 154 (e.g., 154a, 54b). The bottom notch 154b extends the least toward the proximal end of the probe 100 among the first to fourth pairs of notches 151, 152, 153, 154 (e.g., 154a, 54b).

The second pair of second notches 152, which are two side surfaces among the three surfaces of the treatment surface 145, on opposite sides of the top notch 154a, extend second furthest toward the proximal end of the probe 100 among the first to fourth pairs of notches 151, 152, 153, 154 (e.g., 154a, 154b). The first pair of notches 151 extend third furthest toward the proximal end of the probe 100 among the first to fourth pairs of notches 151, 152, 153, 154 (e.g., 154a, 154b). The third pair of notches 153, which are two side surfaces among the three surfaces of the opposite surface 146, on opposite sides of the bottom notch 154b, extend fourth furthest toward the proximal end of the probe 100 among the first to fourth pairs of notches 51, 52, 53, 54 (e.g., 54a, 54b).

The distal end 142 of the probe 100 is curved in one direction, e.g., to improve visibility. In the probe 100 according to an embodiment, due to the successively decreasing notch lengths, the length of the successive notches forming the surface of the probe tip becomes shorter from the inside of the curve toward the outside of the curve. As a result, the center of gravity (COG) of the probe 100 moves toward the outside of the curve in the probe 100, i.e., the side of the probe that is facing outward from the curve, as a function of position along the center axis.

Figure 7B:
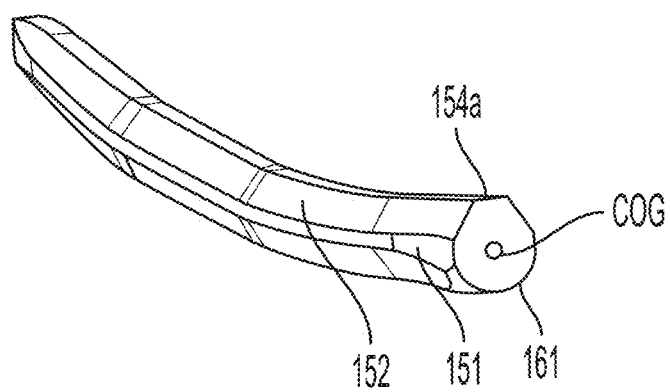
FIG. 7B is a cross-sectional view of the probe of FIG. 6A, taken along line II-II'.
Figure 7C:
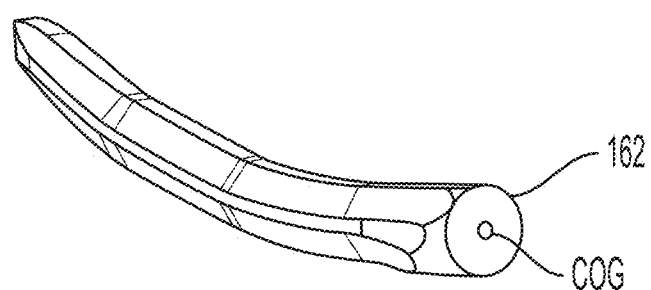
FIG. 7C is a cross-sectional view of the probe of FIG. 6A, taken along line III-III'.

FIG. 7A is a cross-sectional view of the probe of FIG. 6A, taken along line I-I'. FIG. 7B is a cross-sectional view of the probe of FIG. 6A, taken along line II-II'. FIG. 7C is a cross-sectional view of the probe of FIG. 6A, taken along line III-III'.

With reference to FIGS. 7A-7C, each cross section taken along lines I-I', II-II', and III-III' of the probe 100 of FIG. 6A has a different shape. FIG. 7A shows that a most distal cross section, taken along line I-I', closest to the distal end 142, has an octagonal cross section due to the presence of all of the first to fourth pairs of notches 151, 152, 153, 154 (e.g., 154a, 154b). FIG. 7B shows that a middle cross section, taken along line II-II', has a hexagonal (six-sided) cross-section, as only the top notch 154a, the second pair of notches 152, and the first pair of notches 151 are present in the middle section. The bottom of the hexagon is a curve 161. FIG. 7C shows that a most proximal cross section, taken along line I-I', closest to the proximal end 143, has a circular cross section, with no notches present.

Figure 8:
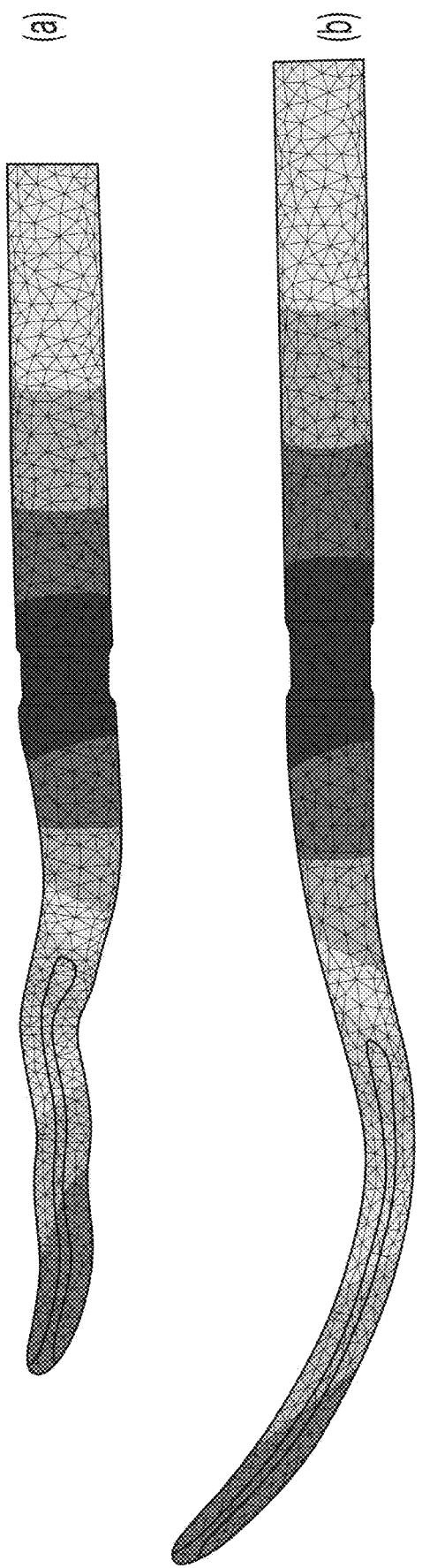
FIG. 8 is a diagram showing strain amounts and directions on the probe of FIG. 6A in a contracted configuration (I) and in an extended, curved configuration (II).

FIG. 8 is a diagram showing strain amounts and directions on the probe of FIG. 6A.

As discussed above, the distal end 142 of the probe 100 is curved in one direction. As shown in FIG. 8, although the forces due to the transverse and twist vibration tend to deform the probe and create an unstable vibration, the effect of transverse and twist vibration on the probe 100 in accordance with an embodiment is less than the effect of transverse and twist vibration that is shown FIG. 5A on the related art probe 24 of FIG. 4A. In an experimental result, with reference to the related art of FIG. 5A being compared to the embodiment of FIG. 8, the probe 100 in accordance with an embodiment has a 39% reduction in transverse vibration, and a 2.3% reduction in twist vibration as compared to the related art probe 24.

Figure 5A:
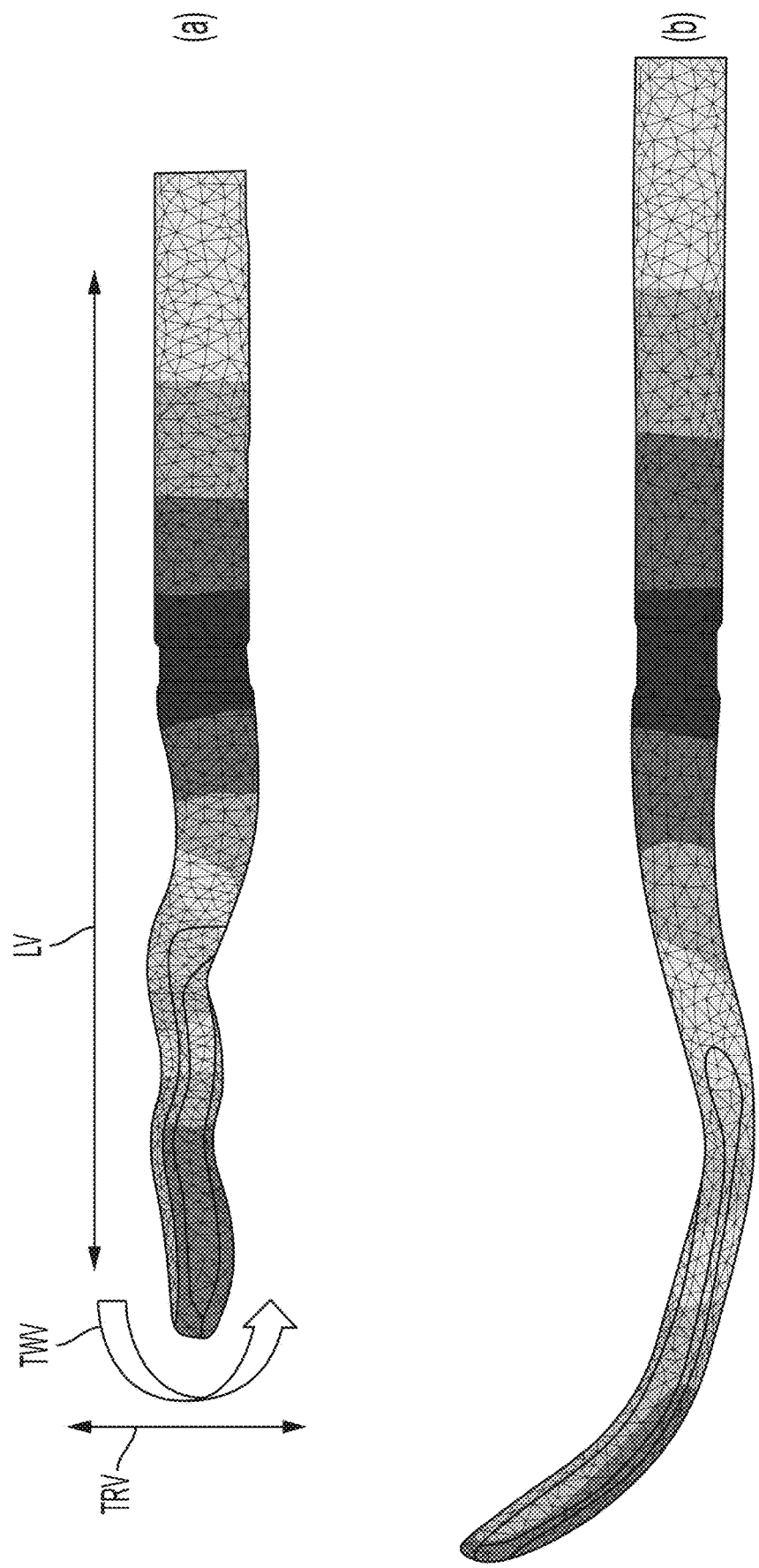
FIG. 5A is a diagram showing strain amounts and directions on the probe of FIG. 4A in a contracted configuration (a) and in an extended, curved configuration (b).
Figure 5B:
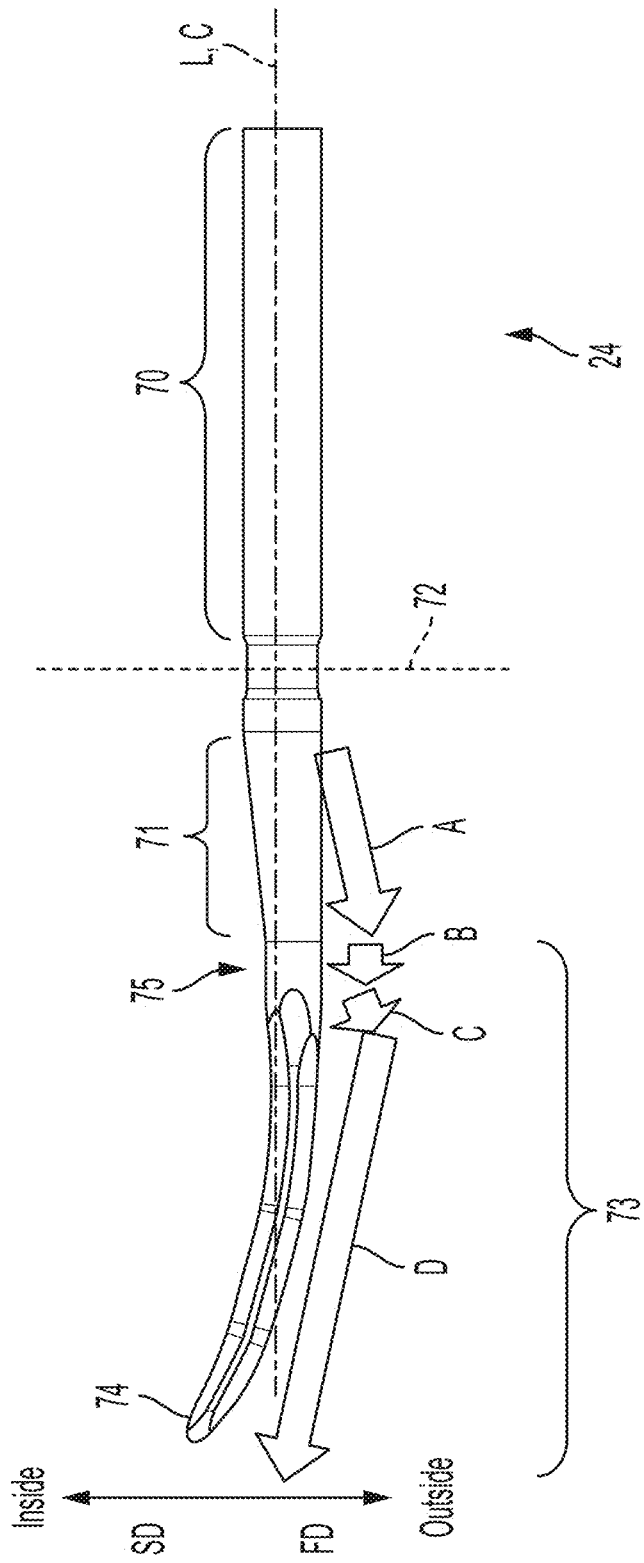
FIG. 5B is another side view of the probe of FIG. 4A and annotating the curvature of the related art probe.
Figure 9:
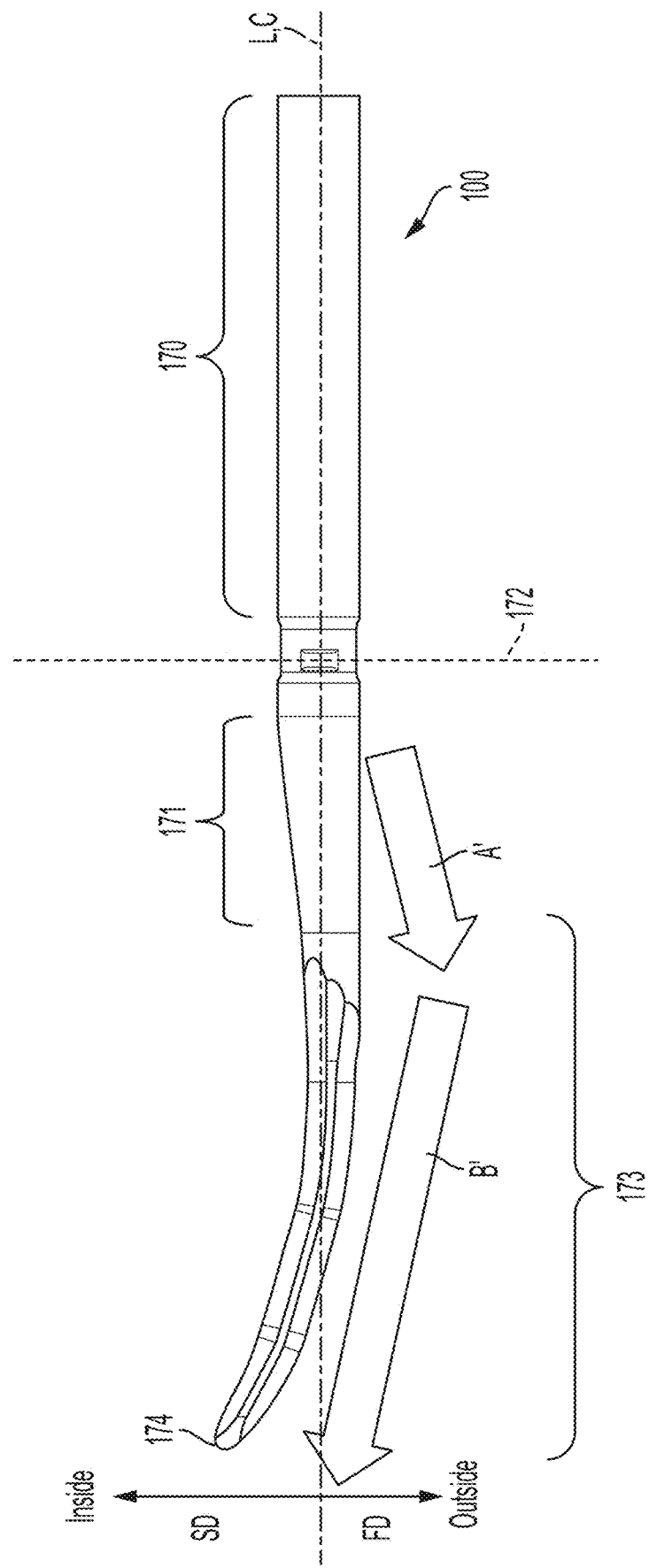
FIG. 9 is another side view of the probe of FIG. 6A and annotating the curvature of the probe.

FIG. 9 is another side view of the probe of FIG. 6A and annotating the curvature of the probe. With reference to FIG. 9, a main body 170 is at the proximal side of the probe 100. A center moving portion 171 of the probe 100 is a taper portion, and is separated from the main body by a node 172. Within the probe 100, the center moving portion 171 is located more distal than the node 172, which itself is at the most distal side of the main body 170, e.g., further toward the distal end. The surface of the center moving portion 171 has a taper portion in which the taper is formed approaching the central axis C toward the distal end, i.e., inwardly (toward the central axis C) and distally (toward the distal end). A curved portion 173 is more distal than the center moving portion 171. The curved portion 173 continues to taper (inwardly and distally) toward the tip 174 of the probe 100. The curvature of the curved portion 173 is a simple curvature, having a continuous curvature, though it can be changing. The continuous curvature is in contrast to the discontinuous curvature in the related art probe 24 of FIG. 5B, which shows curved sections interrupted by non-curved sections. As a result, along the length of the probe 100, the center of gravity of the probe 100 moves relative to the central axis C.

For example, in the center moving portion 171, the center of gravity of the probe 100 moves, e.g., can be measured or determined as a function of position along the center axis, in a first direction (FD), e.g., toward the outside of the curve of the probe 100, as the longitudinal position moves distally from a location proximate the node 172 toward and into a first proximal portion of the center moving portion 171. The taper portion in the configuration described above causes the described movement in the center of gravity in the center moving portion 171. Also for example, in the curved portion 173, the center of gravity of the probe 100 moves (can be measured or determined) in a second direction (SD), e.g., toward the inside of the curve of the probe 100, as the longitudinal position moves distally from the first proximal portion of the center moving portion 171 toward the distal end of the probe 100 at the tip 174. The first to fourth pairs of notches 151, 152, 153, 154 in the configuration described above cause the described movement in the center of gravity in the curved portion 173. In FIG. 9, arrow A' represents the direction and orientation of the movement of the center of gravity of the probe 100 in the center moving portion 171, and arrow B' represents the direction and orientation of the movement of the center of gravity of the probe 100 in the curved portion 173. The movement of the center of gravity is continuous in each of the center moving portion 171 and the curved portion 173. As such, the center of gravity of the probe 100 moves continuously toward the outside of the curve of the probe 100 as the longitudinal position moves distally in the center moving portion 171, and the center of gravity of the probe 100 moves continuously toward the inside of the curve of the probe 100 as the longitudinal position moves distally in the curved portion 173. In other words, eliminating the non-curved section between the between the center moving portion 71 and the first to fourth pairs of notches 151, 152, 153, 154 in the configuration described above results in a first curvature section transitioning directly to a second curvature section, the curvature in the first section being opposite to the curvature in the second section.

Figure 4A:
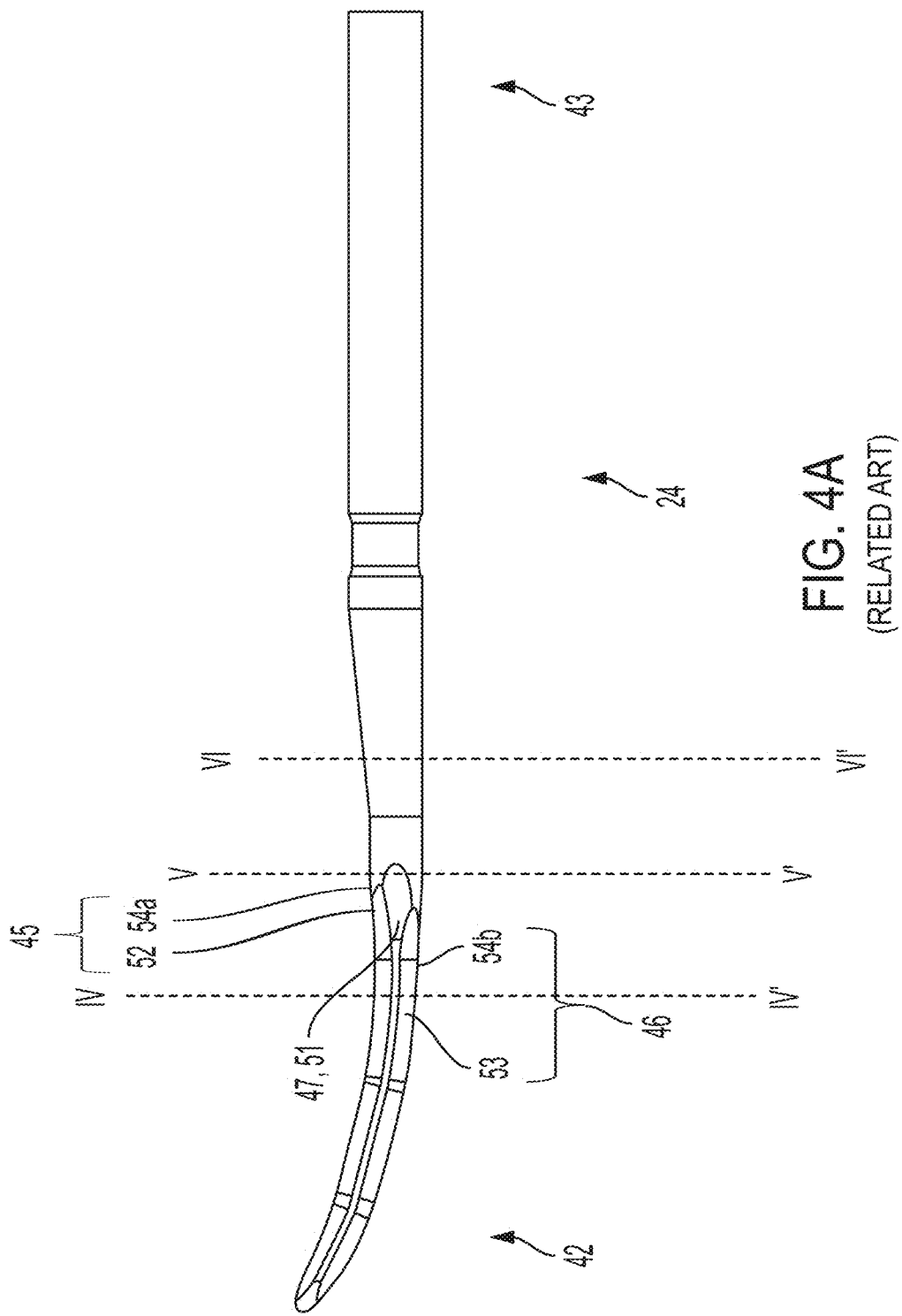
FIG. 4A is a side view of a related art ultrasonic probe in which notches are cut to provide treatment surfaces.
Figure 4B:
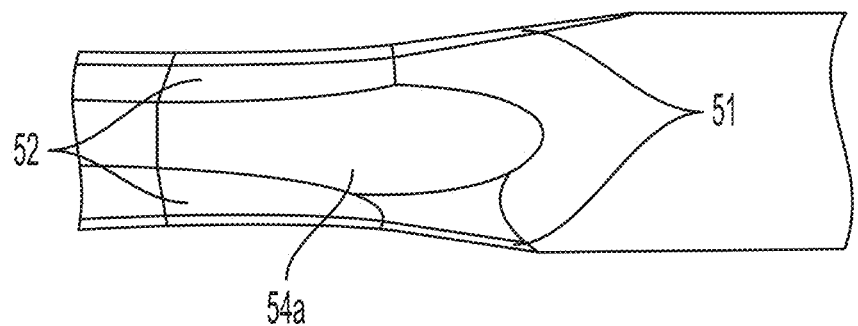
FIG. 4B is a top view of a portion of the probe of FIG. 4A.
Figure 4C:
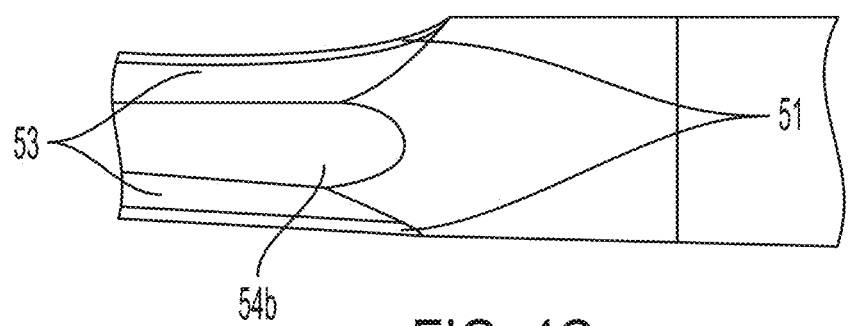
FIG. 4C is a bottom view of a portion of the probe of FIG. 4A.
Figure 10A:
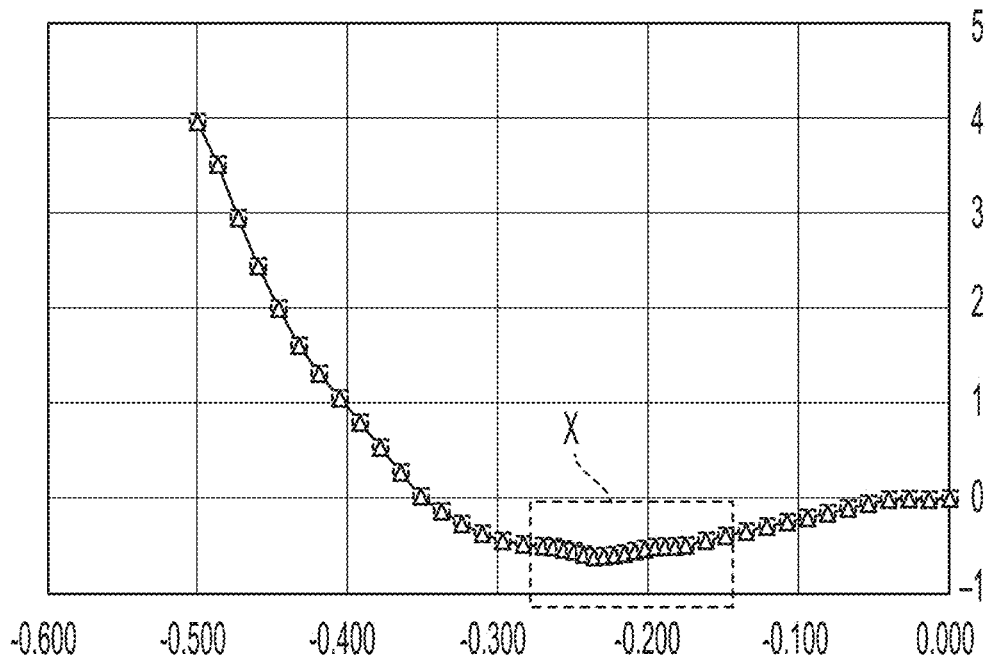
FIG. 10A is a graph showing experimental results of measurement of the center of gravity of the related art probe of FIG. 4A as compared to the probe of FIG. 6A according to an embodiment.
Figure 10B:
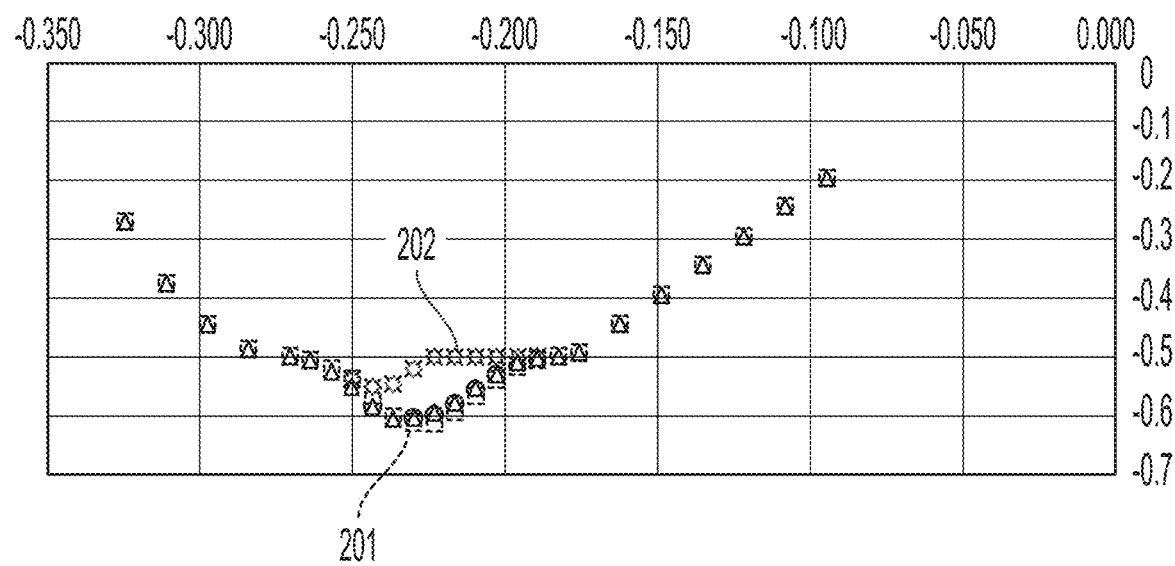
FIG. 10B is an enlargement of a portion X of the graph of FIG. 10A.

FIG. 10A is a graph showing experimental results of measurement of the center of gravity of the related art probe of FIG. 4A as compared to the probe of FIG. 6A according to an embodiment. FIG. 10B is an enlargement of a portion X of the graph of FIG. 10A.

The FIG. 10A graph shows the change of the center of gravity in half wavelength from the distal end toward the proximal end. The measurements of the center of gravity of the related art probe 24 of FIG. 4A is shown as circles. The measurements of the center of gravity of the probe 100 of FIG. 6A according to an embodiment is shown as triangles and squares, with results of two experiments on the probe 100 being overlapped. As can be seen in the detail of FIG. 10B, the center of gravity of the probe 100 moves continuously toward the bottom of the curve, as indicated at reference 201, as shown in the arrows B' and A', in distal to proximal order, in FIG. 9. In contrast, as can be seen in FIG. 10B, the movement of the center of gravity of the related art probe 24 is discontinuous and has a plateau, as indicated at reference 202, before continuing on the curve toward the proximal end defined by arrows D-A, in distal to proximal order, in FIG. 5B.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various example embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described example embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide example instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of example schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A vibration transmission member for an ultrasonic treatment tool, comprising:
   a main body comprising a central axis and having a distal end and a proximal end;
   a center moving portion located at a distal side of a node located where the distal end of the main body meets the center moving portion, the node being at a most distal location of the distal end of the main body; and
   a curved portion located at a distal side of the center moving portion,
   wherein, in a direction from a proximal end of the curved portion toward a distal end of the curved portion, the curved portion is curved in a first direction relative to the central axis,
   wherein the center moving portion has a center of gravity that is located in a cross section of the center moving portion,
   wherein the center moving portion is configured so that as the center of gravity moves along a length of the center moving portion toward the distal end of the center moving portion, the center of gravity moves relative to the central axis in a second direction that is opposite to the first direction,
   wherein the center moving portion extends from the distal end of the main body to the proximal end of the curved portion, and
   wherein the curved portion includes a plurality of notches formed along a periphery of the curved portion.

2. The vibration transmission member of claim 1, wherein a respective length of each of the plurality of notches are equal to each other or becomes shorter depending on a location of each notch.

3. The vibration transmission member of claim 2, wherein the respective length of each of the plurality of notches becomes shorter from the first direction to the second direction.

4. The vibration transmission member of claim 1, wherein the center moving portion has decreased areas of successive cross sections, perpendicular to the central axis, toward the distal end.

5. The vibration transmission member of claim 1, wherein a length of the curved portion along the central axis is longer than a length of the center moving portion along the central axis.

6. The vibration transmission member of claim 1, wherein, in the node, a second notch is provided in a third direction perpendicular to the first direction and the second direction.

7. The vibration transmission member of claim 1, further comprising:
- a treatment surface for performing an ultrasonic treatment, the treatment surface comprising first to third surfaces;
- an opposite surface, opposite to the treatment surface, the opposite surface comprising fourth to sixth surfaces; and
- seventh and eighth surfaces respectively on each side of the curved portion between the treatment surface and the opposite surface, wherein the seventh and eighth surfaces comprise a first pair of notches,
wherein the first and third surfaces comprise a second pair of notches,
wherein the fourth and sixth surfaces comprise a third pair of notches,
wherein the second surface is between the first and third surfaces and comprises a top notch,
wherein the fifth surface is between the fourth and sixth surfaces and comprises a bottom notch,
wherein the top notch extends furthest toward the proximal end among the notches, and
wherein the bottom notch extends least toward the proximal end among the notches.

8. The vibration transmission member of claim 7, wherein the second pair of notches extend second furthest toward the proximal end among the notches.

9. The vibration transmission member of claim 8, wherein the first pair of notches extend third furthest toward the proximal end among the notches.

10. The vibration transmission member of claim 9, wherein the third pair of notches extend fourth furthest toward the proximal end among the notches.

11. The vibration transmission member of claim 7, wherein the first to third notches, the top notch, and the bottom notch are configured to reduce a transverse vibration and a twist vibration in the probe when an ultrasonic vibration is applied to the vibration transmission probe.

12. The vibration transmission member of claim 1, further comprising:
- a distal portion closest to the distal end, the distal portion having a cross section having an octagonal cross section due to the presence of first to fourth pairs of notches, the fourth pair of notches comprising a top notch and a bottom notch;
- a middle portion of the probe having a cross section having a six-sided cross-section, such that only the top notch, the second pair of notches, and the first pair of notches extend from the distal section to the middle section; and
- a proximal portion closest to the proximal end, the proximal portion having a circular cross section, such that no notches extend into the proximal portion.

13. The vibration transmission member of claim 1, wherein the center moving portion comprises a taper portion, the center moving portion being separated from the main body by the node, the center moving portion being located more distal than the node, the node being at the most distal side of the main body toward the distal end, the taper portion in which a taper is formed approaching the central axis of the vibration transmission member toward the distal end, inwardly toward the central axis and distally toward the distal end; and
wherein the curved portion continues to taper, inwardly and distally, toward the tip at the distal end, the curvature of the curved portion being a simple curvature, having a continuous curvature, such that the center of gravity of the vibration transmission member moves relative to the central axis.

14. The vibration transmission member of claim 13, wherein, in the center moving portion, the center of gravity of the vibration transmission member moves, as a function of position along the center axis, in the first direction toward the outside of the curvature of the curved portion, as the longitudinal position moves distally from a location proximate the node toward and into a first proximal portion of the center moving portion.

15. The vibration transmission member of claim 14, wherein, in the curved portion, the center of gravity of the vibration transmission member moves in the second direction toward the inside of the curvature of the curved portion as the longitudinal position moves distally from the first proximal portion of the center moving portion toward the distal end at the tip.

16. The vibration transmission member of claim 15, wherein first to fourth pairs of notches are disposed around the curved portion, the first to fourth pairs of notches being configured to define the movement in the center of gravity in the curved portion.

17. The vibration transmission member of claim 15, wherein the movement of the center of gravity is continuous in each of the center moving portion and the curved portion.

18. The vibration transmission member of claim 17, wherein the center of gravity of the vibration transmission member moves continuously toward an outside of the curvature of the probe as the longitudinal position moves distally in the center moving portion, and continuously toward an inside of the curvature of the probe as the longitudinal position moves distally in the curved portion.

19. An ultrasonic treatment instrument, comprising:
- a handpiece;
- a vibrator detachably attachable to the handpiece, the vibrator comprising:
  - a case, and
  - a vibration generator in the case, the vibration generator being detachably attachable to a housing;
- a power source unit; and
- a cable that connects the handpiece and the power source unit, wherein the handpiece includes:
- the housing forming an outer shell,
- a fixed handle that is provided integrally with the housing,
- a rotatable handle that is rotatable with respect to the housing,
- the vibration transmission member of claim 1 connected to the vibration generator in the case,
- a cylindrically-shaped shaft covering the periphery of the probe in its proximal side to protect the probe,
- a jaw that is rotatable with respect to the vibration transmission member and the shaft, and
- a cylindrically-shaped advance-and-retreat portion that is provided inside the shaft and is caused to advance or retreat when the jaw is opened or closed, wherein one of the two directions parallel to a longitudinal direction of the vibration transmission member is defined as a distal side,
wherein the other direction opposite to the distal side is defined as a proximal side, and wherein the longitudinal direction extends along a central axis of the vibration transmission member.

20. A method of manufacturing a vibration transmission probe for an ultrasonic treatment tool, the method comprising:
   providing a main body comprising a central axis, the main body including a distal end and a proximal end;
   providing a center moving portion at a distal side of a node where the distal end of the main body meets the center moving portion, the node being at a most distal location of the distal end of the main body; and
   providing a curved portion at a distal side of the center moving portion,
wherein, in a direction from a proximal end of the curved portion toward a distal end of the curved portion, the curved portion is curved in a first direction relative to the central axis,
wherein the center moving portion has a center of gravity that is located in a cross section of the center moving portion,
wherein the center moving portion is configured so that, as the center of gravity moves along a length of the center moving portion toward the distal end of the center moving portion, the center of gravity moves relative to the central axis in a second direction that is opposite to the first direction,
wherein the center moving portion extends from the distal end of the main body to the proximal end of the curved portion, and
wherein the curved portion includes a plurality of notches formed along a periphery of the curved portion.

* * * * *